(12) United States Patent
Evens et al.

(10) Patent No.: US 9,381,730 B2
(45) Date of Patent: Jul. 5, 2016

(54) SURROGATE PATCH ASSEMBLY FOR A REWORK AREA OF A COMPOSITE STRUCTURE

(71) Applicant: The Boeing Company, Chicago, IL (US)

(72) Inventors: Michael W. Evens, Burien, WA (US); Megan N. Watson, Kent, WA (US); Mary H. Vargas, Woodinville, WA (US)

(73) Assignee: The Boeing Company, Chicago, IL (US)

( * ) Notice: Subject to any disclaimer, the term of this patent is extended or adjusted under 35 U.S.C. 154(b) by 385 days.

(21) Appl. No.: 14/012,676

(22) Filed: Aug. 28, 2013

(65) Prior Publication Data

US 2014/0000788 A1    Jan. 2, 2014

Related U.S. Application Data

(62) Division of application No. 12/633,753, filed on Dec. 8, 2009, now Pat. No. 8,545,650.

(51) Int. Cl.
| | |
|---|---|
| *B32B 43/00* | (2006.01) |
| *B29C 73/10* | (2006.01) |
| *B29C 73/16* | (2006.01) |
| *G01K 13/00* | (2006.01) |
| *G01N 27/00* | (2006.01) |
| *G01N 33/00* | (2006.01) |

(52) U.S. Cl.
CPC ............ *B32B 43/00* (2013.01); *B29C 73/10* (2013.01); *B29C 73/163* (2013.01); *G01K 13/00* (2013.01); *G01N 27/00* (2013.01); *G01N 33/00* (2013.01)

(58) Field of Classification Search
CPC ........ B29C 73/12; B29C 73/24; B29C 73/10; B29C 73/163; G01N 33/00; G01K 13/00; G01N 27/00; B32B 43/00
USPC ................................ 73/73; 324/71.1; 374/142
See application file for complete search history.

(56) References Cited

U.S. PATENT DOCUMENTS

| | | | |
|---|---|---|---|
| 4,221,962 A * | 9/1980 | Black .................... | G01N 21/431 250/227.25 |
| 4,622,091 A | 11/1986 | Letterman | |
| 4,652,319 A | 3/1987 | Hammond | |

(Continued)

FOREIGN PATENT DOCUMENTS

| | | |
|---|---|---|
| DE | 2007013755 | 3/2008 |
| GB | 2213596 | 8/1989 |
| GB | 2375742 | 11/2002 |

OTHER PUBLICATIONS

Internatinonal Search Report, PCT/US201 01055684, Apr. 20, 2011.

(Continued)

*Primary Examiner* — Lisa Caputo
*Assistant Examiner* — Philip Cotey

(57) ABSTRACT

A surrogate patch assembly for a rework area of a structure comprises a surrogate patch body which may be formed of a material for drawing moisture from the rework area. The patch assembly may include a sensor mounted to the surrogate patch body. The sensor may comprise a thermal sensor for sensing the temperature of the rework area and the surrogate patch body. The sensor may comprise a moisture sensor for sensing moisture drawn into the surrogate patch body.

19 Claims, 10 Drawing Sheets

(56) References Cited

U.S. PATENT DOCUMENTS

| | | | |
|---|---|---|---|
| 4,808,253 A | 2/1989 | Mimbs | |
| 5,053,251 A * | 10/1991 | Hara | C03C 17/02 156/94 |
| 5,145,541 A | 9/1992 | Baron et al. | |
| 5,379,689 A | 1/1995 | Timmons et al. | |
| 5,833,795 A | 11/1998 | Smith et al. | |
| 6,031,212 A | 2/2000 | Westerman et al. | |
| 6,385,836 B1 * | 5/2002 | Coltrin | B29C 70/545 156/285 |
| 6,561,247 B2 | 5/2003 | Chou et al. | |
| 7,089,786 B2 * | 8/2006 | Walker | B65D 79/02 374/E1.003 |
| 2001/0050032 A1 * | 12/2001 | Dry | C04B 22/006 106/677 |
| 2003/0188821 A1 * | 10/2003 | Keller | B29C 43/12 156/94 |
| 2004/0177928 A1 * | 9/2004 | Bivens | B29C 73/34 156/359 |
| 2006/0027308 A1 * | 2/2006 | MacKenzie | B29C 73/30 156/94 |
| 2007/0095457 A1 | 5/2007 | Keller et al. | |
| 2010/0024958 A1 | 2/2010 | Sawicki et al. | |
| 2010/0232963 A1 * | 9/2010 | Volanthen | F03D 1/065 416/146 R |

OTHER PUBLICATIONS

The Engineering ToolBox, "Thermal Conductivity of some Common Materials and Gases," <www.engineeringtoolbox.com/thermal-conductivity-d_429.html]>, retrieved Sep. 24, 2012.

Japanese Office Action, Appl. No. 2012-543112, dated Sep. 1, 2015.

* cited by examiner

SURROGATE PATCH ASSEMBLY FOR A REWORK AREA OF A COMPOSITE STRUCTURE

CROSS-REFERENCE TO RELATED APPLICATIONS

This application claims priority to pending U.S. application Ser. No. 12/633,753, entitled METHOD OF REPAIRING A COMPOSITE STRUCTURE and filed on Dec. 8, 2009, the entire contents of which is incorporated by reference.

FIELD

The present disclosure relates generally to structural repair and, more particularly, to operations performed in preparation for the repair of composite structures.

BACKGROUND

Composite materials are used in ever increasing amounts in a wide variety of applications. For example, commercial aircraft are incorporating increasing amounts of composite materials into primary and secondary structure due to the favorable mechanical properties of composite materials. Such favorable properties may translate into a reduction in weight and an increase in payload capacity and fuel efficiency. In addition, composite materials may provide an extended service life for the aircraft as compared to aircraft formed of metallic construction.

Rework is occasionally required on composite structures in order to remove an inconsistency. An inconsistency may comprise a crack, a delamination, a void, a dent, porosity or other inconsistencies in the composite structure. An inconsistency may require rework when the inconsistency falls outside of desired tolerances. The removal of the inconsistency may require the reworking of an area in the composite structure containing the inconsistency by removing a portion of the composite structure containing the inconsistency and replacing the removed material with a patch. The patch may be formed as a stack of plies of composite material of the same or different type from which the composite structure is formed. The stacking sequence and fiber orientation of the composite plies in the patch may correspond to the stacking sequence and fiber orientation of the plies that make up the composite structure.

After assembling the patch from the stack of plies, the patch is typically bonded to the rework area with adhesive installed at the bondline between the patch and the rework area. Heat and pressure are typically applied to the patch such as with a heating blanket and a vacuum bag. The heating blanket may be used to elevate the bondline to the appropriate adhesive curing temperature. The vacuum bag may be used to consolidate the patch. During curing, the bondline may be held within a relatively narrow temperature range for a predetermined period of time in order to fully cure the adhesive. Furthermore, the entire area of the bondline may be held within the temperature range without substantial variation across the bondline.

Prior to bonding the patch to the rework area, a thermal survey may be required for the rework area. The thermal survey may be required to identify locations of non-uniform heating of the rework area by the heating blanket. Non-uniform heating may be caused by adjacent structure that may act as a heat sink drawing heat away from localized portions of the rework area resulting in differential heating of the bondline. In this regard, the thermal survey may provide a means for identifying hot and cold spots in the rework area such that adjustments can be made by adding temporary insulation to the composite structure and/or by adjusting the heating from the heating blanket until the temperature is within the required range.

A conventional thermal survey process may require assembling a surrogate patch that is a duplicate of the patch that is to be permanently bonded to the composite structure. In this regard, the conventional surrogate patch is formed of the same type of composite material and with the same number of plies as the final patch. Construction of a conventional surrogate patch is a time-consuming and labor-intensive process typically requiring hand-cutting of multiple composite plies each having a unique size and shape for each one of the rework area plies to be replaced. After the thermal survey, the conventional surrogate patch is typically discarded following a single use.

In addition to the thermal survey, a moisture removal process may be required to remove unwanted moisture from the rework area in order to improve the final bond between the patch and the rework area by reducing the risk of porosity within the bondline. A conventional moisture removal process comprises a drying cycle and may be required on composite structure that has been in service for a certain period of time and/or when certain adhesives are used in the repair process.

Unfortunately, the conventional drying cycle typically requires more than 24 hours to complete which may exceed the amount of time that may be available for rework operations performed in the field such as on in-service aircraft. Furthermore, the conventional practice of performing the thermal survey and drying cycle as two separate processes results in the application of two heating cycles on the composite structure which may affect the service life. Even further, the conventional thermal survey requires the labor-intensive and time-consuming process of fabricating the conventional surrogate patch after which the surrogate patch is discarded following a single use. In this regard, the materials for forming the composite surrogate patch may be relatively costly depending upon the amount and type of material used.

As can be seen, there exists a need in the art for a system and method for performing a thermal survey which obviates the need for fabricating a duplicate of the final patch. Furthermore, there exists a need in the art for a system and method for performing a moisture removal process on a rework area on composite structure that avoids the application of an additional heat cycle on the composite structure.

SUMMARY

The above-noted needs associated with the thermal survey and moisture removal of rework areas of composite structure are addressed by providing a surrogate patch assembly that obviates the need for a duplicate of the final patch. The surrogate patch assembly may facilitate the rework of the structure by including a surrogate patch body formed of a material for drawing moisture from the rework area. The surrogate patch body may include at least one sensor mounted to the surrogate patch body. The sensor may be configured as a thermal sensor for sensing a temperature of at least the rework area and/or the surrogate patch body. The sensor may also be configured as a moisture sensor for sensing moisture that has been drawn from the rework area by the material of the surrogate patch body.

In a further embodiment, disclosed is a surrogate patch assembly for a rework area of a composite structure wherein the surrogate patch assembly comprises a surrogate patch body having top and bottom surfaces and defining a substantially uniform thickness. The surrogate patch body may be formed of felt for drawing moisture from the rework area. The felt may have a thermal conductivity of approximately 0.01 to 1.0 W/mK and a specific heat capacity of approximately 600 to 1100 J/(kgK). The surrogate patch assembly may include a plurality of thermal sensors mounted to the surrogate patch body for sensing a temperature of the rework area and the surrogate patch body. At least one of the thermal sensors may be embedded within the surrogate patch body between the top and bottom surfaces. A plurality of moisture sensors may be mounted to the surrogate patch body on the top surface for sensing moisture absorbed from the rework area.

Also disclosed is a surrogate patch system for repairing a structure with a patch that is receivable within a rework area. The surrogate patch system may comprise a surrogate patch body formed of non-composite material having thermal properties that may be substantially similar to thermal properties of the patch. The thermal properties may comprise specific heat capacity and/or thermal conductivity. The surrogate patch system may include at least one thermal sensor mounted to the surrogate patch body for sensing a temperature thereof. The surrogate patch system may include at least one moisture sensor for sensing moisture drawn from the rework area. In addition, the surrogate patch system may include at least one thermal sensor mounted on the rework area for sensing a temperature thereof.

In addition, disclosed is a method of repairing a composite structure having upper and lower surfaces. The method may comprise the steps of forming a surrogate patch body of material for drawing moisture from a rework area of the composite structure. The method may include mounting at least one sensor on the surrogate patch body and mounting at least one thermal sensor in the rework area. The surrogate patch body may be installed in the rework area. The method may include performing at least one of a thermal survey of the rework area and/or removal of moisture from the rework area into the surrogate patch body.

In a further embodiment, disclosed is a method of repairing a composite structure having upper and lower surfaces. The method may comprise the steps of forming a surrogate patch body of material for drawing moisture from a rework area of the composite structure. The material may have a specific heat capacity and a thermal conductivity that may be substantially similar to the specific heat capacity and thermal conductivity of the patch. The method may further include mounting a thermal sensor on the surrogate patch body for sensing a temperature of at least one of the rework area and the surrogate patch body. The method may also include mounting a moisture sensor on the surrogate patch body for sensing moisture drawn from the rework area. A thermal sensor may also be mounted on the upper surface of the composite structure opposite a location of the heat sink on the lower surface. A thermal sensor may be mounted on a bottom center and/or on a scarf of the rework area.

The method may further include covering the rework area with a parting film and installing the surrogate patch body in the rework area over the parting film. The method may also include covering the surrogate patch body with a porous parting film and breather layer, installing a heating blanket over the breather layer, and installing a breather layer over the heating blanket. The surrogate patch body and heating blanket may be vacuum bagged to the upper surface of the structure with a bagging film. The rework area may be heated and a vacuum may be drawn on the bagging film. The method may include performing at least one of a thermal survey of the rework area and/or removal of moisture from the rework area.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
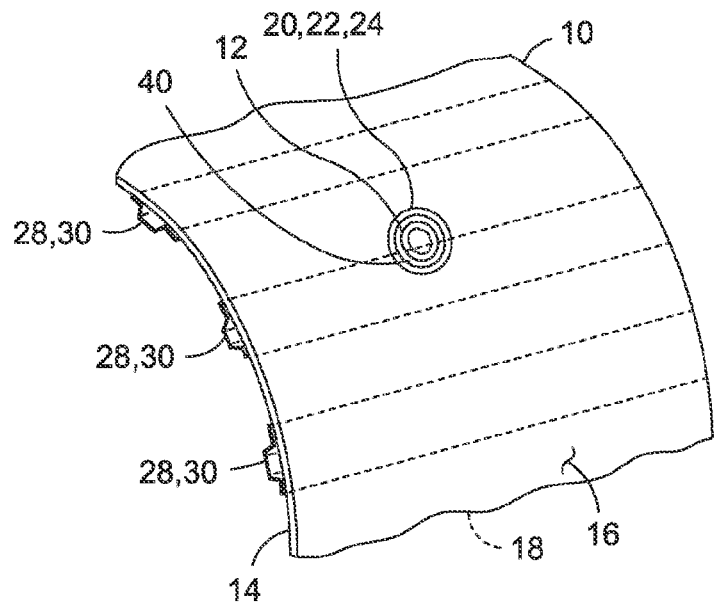
FIG. 1 is a perspective illustration of a portion of a composite structure having a rework area formed therein.

Referring now to the drawings wherein the showings are for purposes of illustrating preferred and various embodiments of the disclosure only and not for purposes of limiting the same, shown in FIG. 1 is a perspective illustration of a composite structure 10 upon which a repair process may be implemented using a surrogate patch assembly as illustrated in FIGS. 4-9. More specifically, the preparation of a rework area 20 may include a thermal survey and/or a moisture removal process which may employ the surrogate patch assembly 50 (FIGS. 4-9) as disclosed herein and which may be fabricated of low-cost material in a relatively short period of time as will be described in greater detail below.

Figure 2:
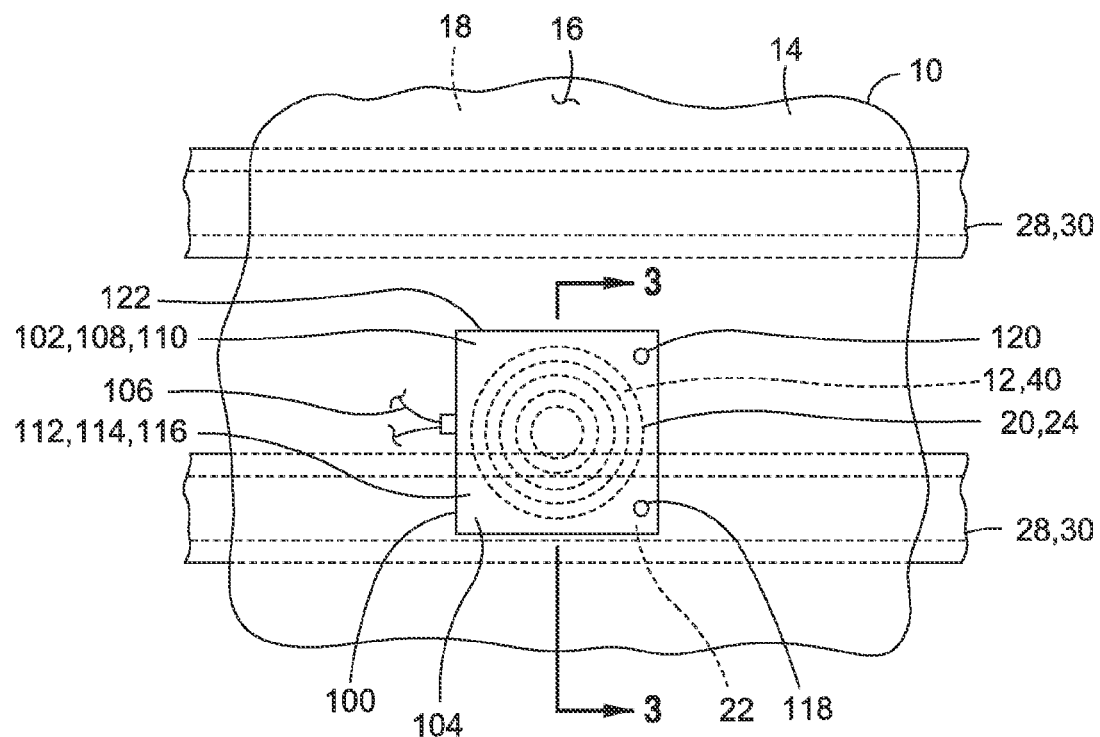
FIG. 2 is a top view illustration of a composite structure having a vacuum bag assembly and heating blanket installed over a patch mounted within the rework area.
Figure 3:
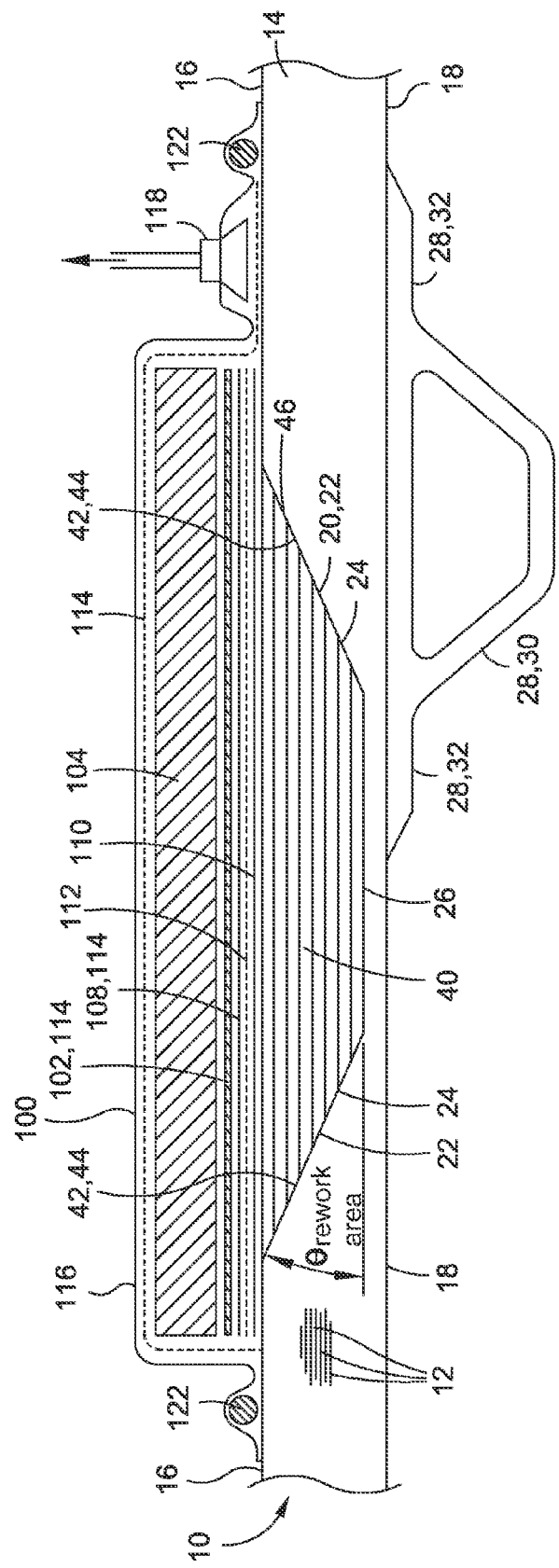
FIG. 3 is a sectional illustration of the vacuum bag assembly mounted to the composite structure taken along line 3-3 of FIG. 2 and illustrating a heat sink comprising a stringer located on a lower surface of the composite structure opposite a portion of the rework area.

In FIG. 1-2, the composite structure 10 may include a skin 14 formed of plies 12 of composite material and wherein the skin 14 may have upper and lower surfaces 16, 18. The composite structure 10 may include the rework area 20 formed in the skin 14 and from which composite material may be removed in preparation for receiving a patch 40. As can be seen in FIG. 3, the rework area 20 may be formed in the upper surface 16 and may extend at least partially through the skin 14 although the rework area 20 may be formed in the lower surface 18 and/or may extend through a thickness of the skin 14. Various heat sinks 28 may be mounted to the lower surface 18 opposite the rework area 20 such as, without limitation, stringers, stiffeners, and spars which may draw heat away from the rework area 20 during the repair.

For example, FIGS. 2-3 illustrate a stringer 30 mounted to a lower surface 18 and having flanges 32 that extend along a portion of the rework area 20 on a right-hand side thereof and which may draw heat away from the rework area 20. The remainder of the rework area 20 may lack any structure which would otherwise draw heat away from the rework area 20. In this regard, the thermal survey may assist in identifying locations of a bondline 46 (FIG. 3) between the patch 40 and the rework area 20 that require a greater amount of heat input relative to other areas of the bondline. The thermal survey may also assist in identifying locations of the rework area 20 that may require the temporary application of insulation to the composite structure 10 in order to attain substantial temperature uniformity throughout the bondline 46 (FIG. 3).

Shown in FIGS. 2-3 is a vacuum bag assembly 100 for use during the final repair process or during pre-repair operations of the thermal survey and/or moisture removal process. The vacuum bag assembly 100 may comprise a heating blanket 104 or other heating equipment. The heating blanket 104 may include wiring 106 coupled to a power source (not shown) for heating the rework area 20 to the desired temperature during the thermal survey or moisture removal process. The vacuum bag assembly 100 may include a bagging film 116 covering the heating blanket 104 and may be sealed to the upper surface 16 of the composite structure 10 by means of sealant 122 tape. A vacuum probe 118 may extend from the bagging film 116 to provide a means for evacuating volatiles, air and/or gas from the rework area 20.

As shown in FIG. 3, the vacuum bag assembly 100 may comprise a caul plate 102 positioned above a non-porous parting film 108 (e.g., peel ply) to facilitate the application of uniform pressure to the patch 40. The parting film may prevent adhesion of the caul plate 102 to layers directly below the caul plate 102. The parting film may, in turn, be positioned over a porous bleeder layer 112 which may be positioned over a porous parting film 110 to facilitate the escape of volatiles during the bonding of the patch 40 to the composite structure 10. The patch 40 may be received within the rework area 20 and may include a scarf 44 formed on the patch edge 42 and substantially matching the scarf 24 formed at a rework taper angle $\theta_{rework\ area}$ of the rework area 20. The surrogate patch body 52 may include a plurality of plies corresponding to the plies 12 of the composite structure 10.

Figure 4:
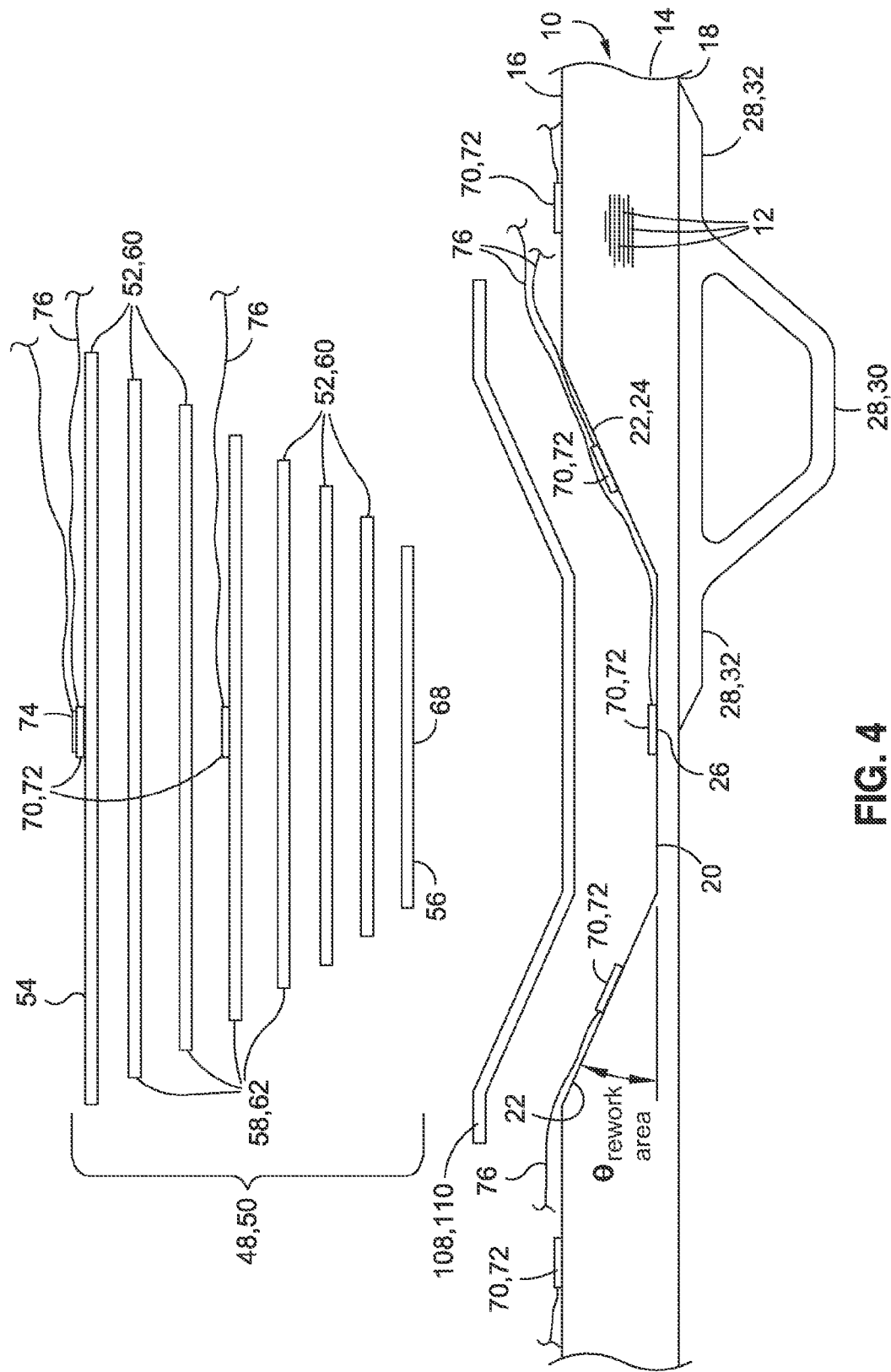
FIG. 4 is an exploded sectional illustration of a surrogate patch system comprising a surrogate patch body formed as a plurality of layers arranged in stacked formation.

Referring to FIG. 4, shown is a surrogate patch assembly 50 as may be used for conducting a thermal survey and/or moisture removal from the rework area 20 prior to final bonding of the patch to the rework area 20. As can be seen in FIG. 4, the surrogate patch assembly 50 may comprise a surrogate patch body 52 which may be formed of a material for drawing moisture from the rework area 20. The material may comprise a non-composite material including natural and/or synthetic material such as, without limitation, wool, cotton, silk, linen, polyester, nylon and acrylic and any other material or combination thereof. However, it is also contemplated that embodiments of the surrogate patch body may include composite material such as, without limitation, fiber-reinforced polymeric materials.

The surrogate patch assembly 50 may further include one or more sensors such as a thermal sensor 70 which may be mounted to the surrogate patch body 52 for sensing temperature of the rework area 20 during a thermal survey. The sensor may also comprise a moisture sensor 74 for sensing moisture that may be drawn from the rework area 20 into the surrogate patch body 52 during the moisture removal process. The thermal sensor 70 may comprise any suitable temperature measuring instrumentation including, but not limited to, thermocouples 72 and any other suitable elements for sensing the temperature of the rework area 20 and/or the surrogate patch body 52.

As was indicated above, the surrogate patch body 52 of the surrogate patch assembly 50 is preferably formed of a material that possesses thermal properties similar to the composite material from which the final patch 40 (FIG. 3) is formed. In this regard, the surrogate patch body 52 is preferably formed of a material that has a specific heat capacity and/or a thermal conductivity that is substantially equivalent to the specific heat capacity and thermal conductivity of the patch. The thermal conductivity of the patch is preferably measured in the transverse out-of-plane direction in order to simulate the direction along which heat may flow during the repair process.

The patch 40 (FIG. 3), in an embodiment, may be fabricated from epoxy pre-impregnated carbon fiber tape and/or fabric. However, the composite material from which the patch may be formed may comprise any suitable pre-impregnated or wet layup composite material and is not limited to the materials disclosed herein. The specific heat capacity, thermal conductivity and other thermal properties of the composite material are preferably those properties exhibited by the composite material when fully cured and at a specific or certain fiber volume content and density. For the above-mentioned epoxy pre-impregnated carbon fiber tape material having a fiber volume content of 0.56 and a density of 5.64E−2 lb/in$^3$, the thermal properties may comprise a thermal conductivity in the range of from approximately 0.01 W/mK to approximately 1.0 W/mK wherein such properties are measured at a temperature $T_0$ of approximately 20° C. (i.e., room temperature).

In this regard, the surrogate patch body 52 may be formed of a material having a thermal conductivity similar to the above mentioned range of 0.01 W/mK to approximately 1.0 W/mK. In an embodiment, the thermal conductivity of the surrogate patch body 52 may be approximately 0.04 W/mK. However, the surrogate patch body 52 may be formed of a material having any thermal conductivity which is complementary to or substantially equal to the thermal conductivity of the material from which the patch 40 (FIG. 3) is formed. Advantageously, by forming the surrogate patch body 52 of the material having a thermal conductivity that is substantially similar to the thermal conductivity of the composite material of the patch, the heating characteristics of the patch may be substantially duplicated without the need for fabricating a conventional surrogate patch of individually-cut composite plies as described above. In this regard, the expense and time normally associated with conventional surrogate composite patches can be substantially reduced.

The surrogate patch body 52 may be formed of a material which may have a specific heat capacity that is preferably in the range of the specific heat capacity of the composite material from which the patch 40 (FIG. 3) may be formed. For example, the surrogate patch body 52 may be formed of material having a specific heat capacity in the range of from approximately 600 J/(kgK) to approximately 1100 J/(kgK) and preferably approximately 830 J/(kgK) measured at a temperature $T_0$ of approximately 273K (i.e., room temperature). As was indicated above, such specific heat capacity and thermal conductivity represent the specific heat capacity and thermal conductivity of the epoxy pre-impregnated carbon fiber tape and/or fabric from which the patch may be formed and are not to be construed as limiting alternative thermal properties of the surrogate patch assembly 50.

Referring still to FIG. 4, in an embodiment, the surrogate patch body 52 material may be formed of natural or synthetic material or any combination thereof. For example, the material from which the surrogate patch body 52 may be formed may comprise wool, cotton, silk, linen, polyester, nylon and acrylic or any other suitable material which may substantially duplicate the thermal properties (i.e., specific heat capacity and thermal conductivity) of the material from which the final patch may be formed. In one embodiment, the material may comprise a non-woven material or fabric which may be comprised of bonded fibers. For example, the surrogate patch body 52 may be formed of felt due to its favorable wicking properties and favorable thermal insulating properties. The wicking properties of felt are such that fluid may be drawn away from the rework area 20 and into the surrogate patch body 52 due to capillary action in the felt material. The thermal conductivity of wool felt, in an embodiment, is approximately 0.04 W/mK which may be compatible with the thermal conductivity of composite materials from which the patch may be formed.

Although the surrogate patch body 52 may preferably be formed of felt, the surrogate patch body 52 may be formed of any suitable material that may draw moisture from the rework area 20 when the surrogate patch body 52 is placed into contact therewith. For example, the surrogate patch body 52 may be formed of alternative materials such as woven materials having high absorbency at elevated temperatures similar to the curing temperatures associated with composite repair. In this regard, the surrogate patch body 52 material is preferably such that heat such as from a heating blanket 104 penetrates the thickness of the surrogate patch body 52 to facilitate an accurate measurement of the temperature at the bondline 48 between the surrogate patch body 52 and the rework area 20.

Referring still to FIG. 4, the surrogate patch body 52 may be formed of a plurality of layers 60 which may be arranged in stacked formation. The patch assembly layers 60 may be formed such that the layer edges 62 collectively define a taper angle which is substantially similar to the rework taper angle $\theta_{rework\ area}$ as illustrated in FIG. 4. Although shown as having a generally tapered arrangement wherein the layers 60 are of a decreasing width and/or diameter, the layers 60 of the surrogate patch body 52 may be of substantially equivalent width such that when the layers 60 are assembled in the stacked arrangement, the layer edges 62 are in substantial alignment with one another. In this regard, the assembled surrogate patch body 52 may comprise the plurality of layers 60 that may be received within the rework area 20.

In FIG. 4, the surrogate patch assembly 50 may be separated from the rework area 20 by a parting film which may be a non-porous parting film 108 or a porous parting film 110. The surrogate patch assembly 50 may include one or more thermal sensors 70 mounted at strategic locations on the rework area 20 in order to monitor temperatures at such locations of the rework area 20 during the application of heat. As part of a conventional thermal survey, thermal sensors 70 such as thermocouples 72 may be installed at a bottom center 26 of the rework area 20 and on a taper of the boundary 22 of the rework area 20 in order to monitor the temperature profile.

Likewise, the surrogate patch body 52 may include one or more thermal sensors 70 in order to measure temperatures during the thermal survey.

For example, the surrogate patch body 52 may include a thermal sensor 70 mounted on a top surface 54 such as at a center thereof as illustrated in FIG. 4. A thermal sensor 70 may also be mounted within the surrogate patch body 52 such as between the top and bottom surfaces 54, 56. In this regard, fabrication of the surrogate patch body 52 as a stack of layers 60 may facilitate installation of thermal sensors 70 at different locations within the surrogate patch body 52. The thermal sensors 70 may also be arranged along a perimeter 58 of the surrogate patch body 52. The sensors may be attached to the surrogate patch body 52 by any suitable means including, but not limited to, bonding and mechanical attachment. Notably, the thermal sensors 70 may be mounted at any location within the rework area 20 such as on the rework area 20 scarf 24 or at the bottom center 26 of the rework area 20 or at locations that are opposite the location of heat sinks such as the stringer 30 that may at least partially overlap a portion of the rework area 20.

The surrogate patch assembly 50 may further include the moisture sensors 74 for sensing the presence of moisture and/or the relative content of moisture which may be contained within the rework area 20. The moisture sensors 74, in an embodiment, may comprise conventional moisture detection strips such as, without limitation, cobalt chloride moisture detection strips or other chemical composition moisture detection strips which may change color in the presence of a sufficiently high level of moisture or water. However, any suitable sensor configuration for detecting the presence of moisture such as water may be implemented into the surrogate patch assembly 50. For example, the moisture sensor 74 may comprise sensors which operate using electrochemical impedance spectroscopy (EIS) or any other suitable sensing technology. The moisture sensors 74 may be selectively configured to provide an indication (e.g., a visual indication) regarding the presence of moisture in the surrogate patch body 52 which may be drawn from the rework area 20. Such moisture may be drawn from the rework area 20 when the surrogate patch body 52 is in contact therewith and/or during the application of heat. The moisture sensors 74 are preferably mounted in a suitable arrangement on the surrogate patch body 52 such as in spaced relation to one another along the top surface 54 of the surrogate patch body 52 as illustrated in FIG. 6 and described in greater detail below.

Figure 5:
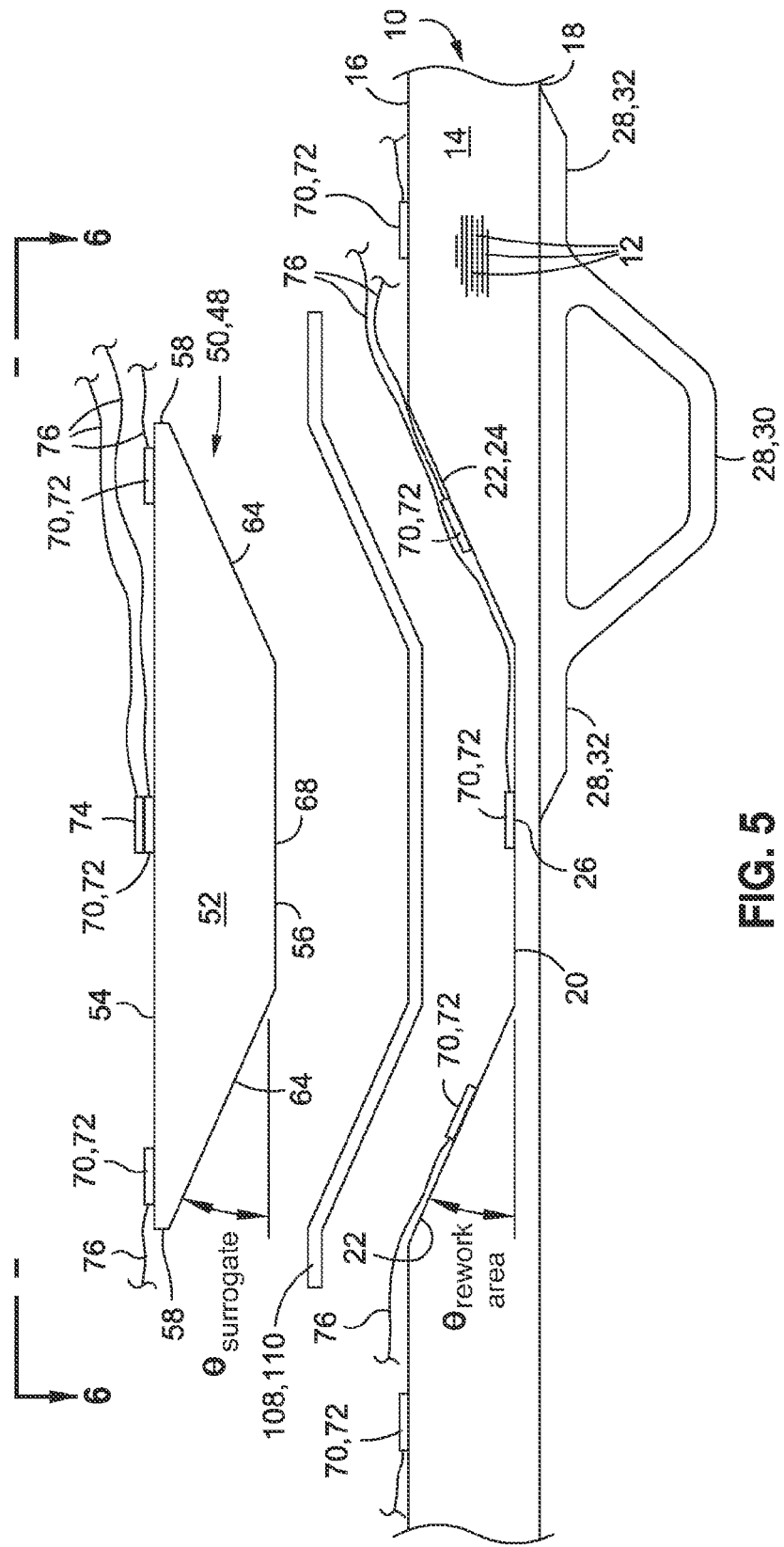
FIG. 5 is an exploded sectional illustration of the surrogate patch body formed as a unitary structure.

Referring to FIG. 5, shown is the surrogate patch assembly 50 wherein the surrogate patch body 52 is provided in an embodiment comprising a unitary structure of a single layer or ply as opposed to the arrangement of layers 60 illustrated in FIG. 4. In FIG. 5, the surrogate patch body 52 may be formed as a thickness that approximates the thickness of the rework area 20 into which the surrogate patch body 52 is received. Furthermore, the perimeter 58 of the surrogate patch body 52 may include a scarf 64 formed at a patch taper angle $\theta_{surrogate}$ which is preferably complementary to the rework taper angle $\theta_{rework\ area}$ such that the surrogate patch body 52 is received in intimate contact with the rework area 20. As was indicated earlier, the surrogate patch body 52 may be separated from the rework area 20 by porous or non-porous parting film 108 such as fluorinated ethylene propylene (FEP) or other similar heat resistant and/or non-sticking material to allow release of the surrogate patch body 52 from the rework area 20 following completion of the thermal survey and/or moisture removal process. As can be seen in FIG. 5, the thermal sensors 70 may be mounted to the rework area 20 in the areas noted as well as in areas adjacent to the rework area 20 and may be coupled to instrumentation (not shown) such as a data acquisition system (not shown) by means of sensor wiring 76 or by wireless means. Likewise, the thermal sensors 70 and/or moisture sensors 74 mounted on the surrogate patch body 52 may be coupled to instrumentation by means of sensor wiring 76 to facilitate measuring and recording of temperature and/or moisture within the surrogate patch body 52.

Figure 6:
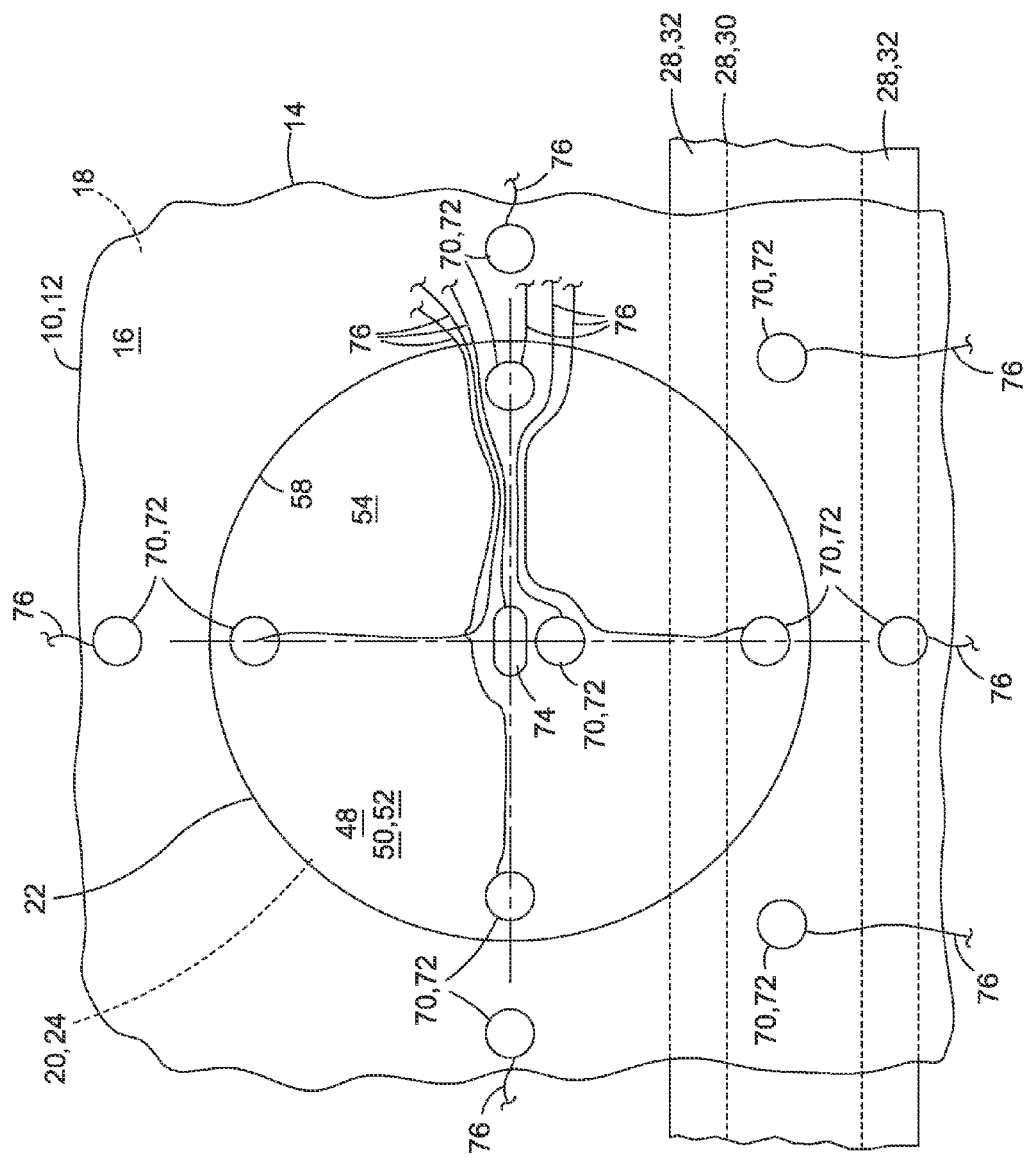
FIG. 6 is a top view illustration of the surrogate patch assembly taken along line 6-6 of FIG. 5 and illustrating a plurality of thermal sensors and moisture sensors mounted to the surrogate patch body and composite structure.

Referring to FIG. 6, shown is a plan view of an installation of thermocouples 72 and/or moisture sensors 74 on the surrogate patch body 52 and on the composite structure 10 adjacent to the rework area 20. As can be seen, thermal sensors 70 may be located on the top surface 54 of the composite structure 10 opposite the stringer 30 which may draw heat away from the rework area 20. The thermal sensors 70 may provide a means for monitoring temperature to indicate that insulation may be required on the stringer 30 or that separate heating of the stringer 30 or areas adjacent thereto may be required in order to heat up the rework area 20 at the desired rate and maintain the patch within the desired temperature range. As can be seen, the surrogate patch body 52 may include one or more moisture sensors 74 such as the moisture sensor 74 located at the center of the surrogate patch body 52. However, moisture sensors 74 may be distributed along the top surface 54 of the surrogate patch body 52 to facilitate the identification of areas in the rework area 20 from which moisture is drawn. The thermal sensors 70 and/or moisture sensors 74 may provide data regarding a thermal profile and/or moisture profile of the rework area 20.

Figure 7:
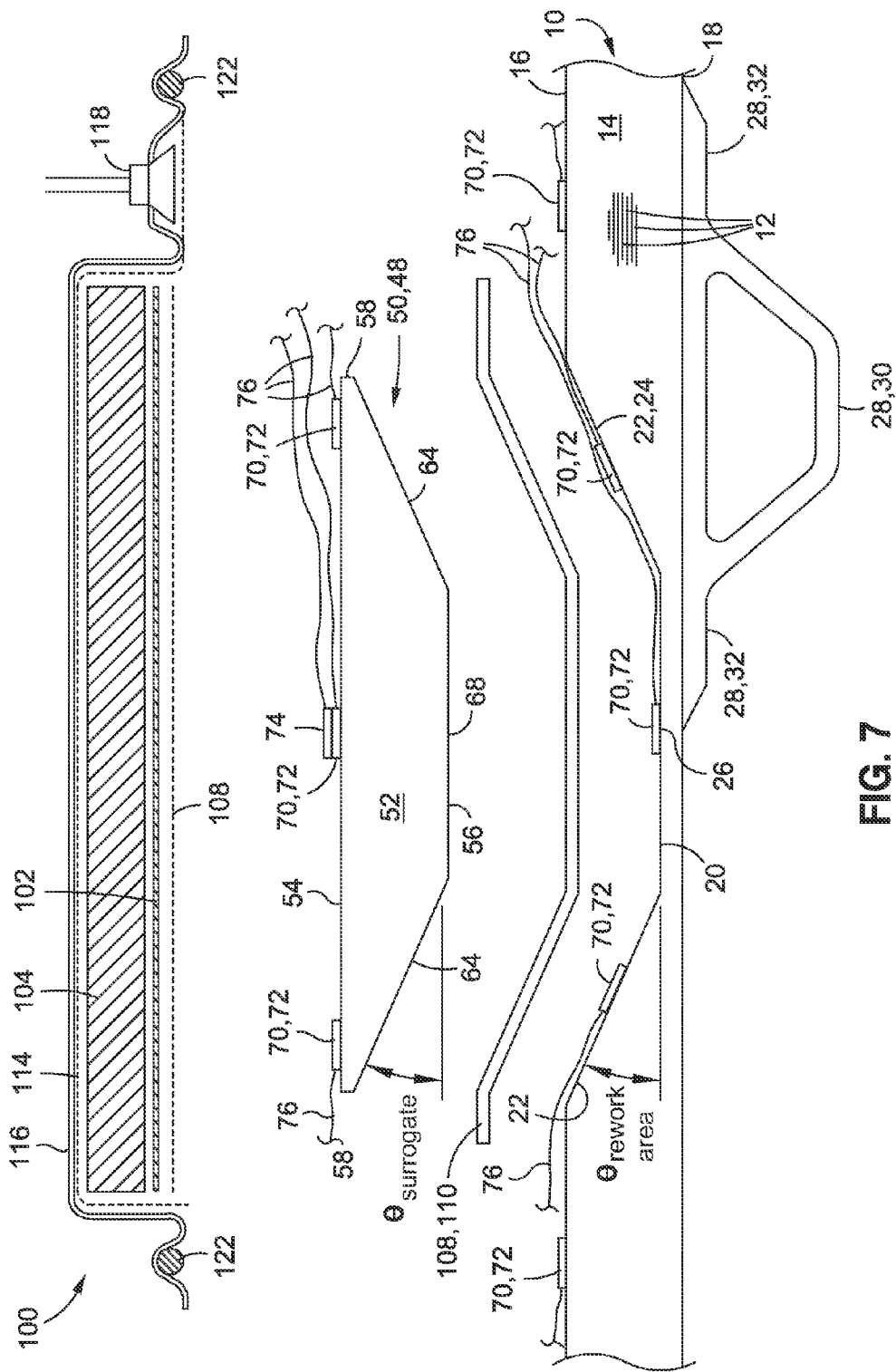
FIG. 7 is an exploded sectional illustration of the vacuum bag assembly as may be installed over the surrogate patch assembly for conducting a thermal survey of the rework area.

Referring to FIG. 7, shown is the surrogate patch system 48 which may comprise the surrogate patch assembly 50 and which may further include a vacuum bag assembly 100 comprising a bagging film 116 enveloping a heating blanket 104 which may cover the patch assembly when installed within the rework area 20. As can be seen in FIG. 7, the surrogate patch body 52 may be separated from the rework area 20 by means of the porous and/or non-porous parting film 110, 108 depending on whether the thermal survey may include a moisture removal process. As mentioned above, the surrogate patch assembly 50 as disclosed herein provides a means for combining the thermal survey and moisture removal such that a single heat cycle is imposed on the composite structure 10. The vacuum bag assembly 100 can be seen as including the bagging film 116 which may be sealed to the top surface 54 of the composite structure 10 by means of sealant 122 such as tape sealant 122 conventionally used in vacuum bagging operations.

The bagging film 116 may envelope a breather layer 114 which may cover a heating blanket 104 and which may extend on one or both sides of the heating blanket 104 to the sealant 122 area. The breather layer 114 may extend underneath a vacuum probe 118 which may be disposed on a side of the heating blanket 104 in order to facilitate the substantially uniform application of vacuum pressure on the surrogate patch body 52 during the thermal cycling and/or moisture removal process. A caul plate 102 may be positioned underneath the heating blanket 104 in order to provide uniform application of pressure to the surrogate patch body 52. The caul plate 102 may be formed of any suitable rigid or semi-rigid material including, but not limited to, a rubber caul material such as cured silicon rubber sheet and/or a metallic material or any combination of metallic and nonmetallic materials. The caul plate 102 may be separated from the surrogate patch body 52 by means of the parting film which may be formed of any suitable material for preventing adhesion or contact of the caul plate 102 with the rework area 20 and/or surrogate patch body 52. For example, the parting film may be perforated (i.e., porous) or non-perforated (i.e., non-porous) and may be formed of any suitable material including fluorinated ethylene propylene (FEP), or any other suitable material.

Figure 8:
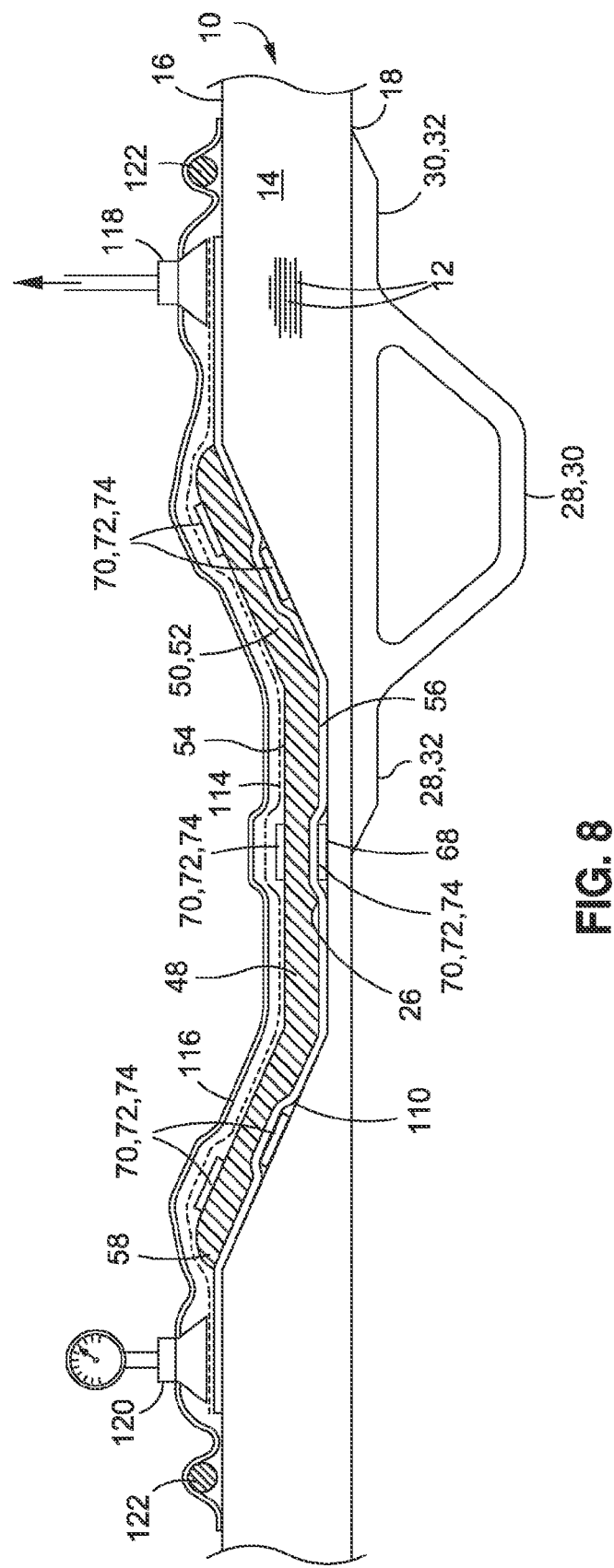
FIG. 8 is a sectional illustration of an embodiment of the surrogate patch assembly mounted within the rework area under application of a vacuum during a moisture removal process.

Referring to FIG. 8, shown is a cross-sectional illustration of the surrogate patch body 52 having the vacuum bag mounted thereto without the heating blanket 104. Such an arrangement may be implemented during a moisture removal process. Optionally, the assembly may be installed in an oven or autoclave to facilitate the application of heat to the composite structure 10. As can be seen in FIG. 8, the vacuum bag includes the vacuum probe 118 for drawing gasses out of the area enveloped by the bagging film 116. A vacuum gauge 120 on an opposite side of the vacuum bag assembly 100 provides a means for monitoring vacuum pressure within the vacuum bag. The surrogate patch body 52 can be seen as having a substantially uniform thickness.

The surrogate patch body 52 may be formed of any one of the above-mentioned materials. In this regard, the surrogate patch body 52 may be formed of a flexibly resilient material capable of conforming to the contour or shape of the rework area 20 in three-dimensions. The perimeter 58 of the surrogate patch body 52 can be seen as conforming or partially compressing under pressure from the vacuum bag. The surrogate patch body 52 may be separated from the bagging film 116 by a breather layer 114 to allow for the escape of moisture. The surrogate patch body 52 may be separated from the rework area 20 by means of a porous parting film 108 to prevent contact therebetween while allowing moisture to escape from the rework area 20. Thermocouples 72 or other thermal sensors 70 may be installed at strategic locations within the rework area 20 as illustrated in FIG. 8 and described above. Likewise, the surrogate patch body 52 may include thermal sensors 70 and/or moisture sensors 74 at locations along the surrogate patch body 52 for monitoring temperature and moisture removal.

Figure 9:
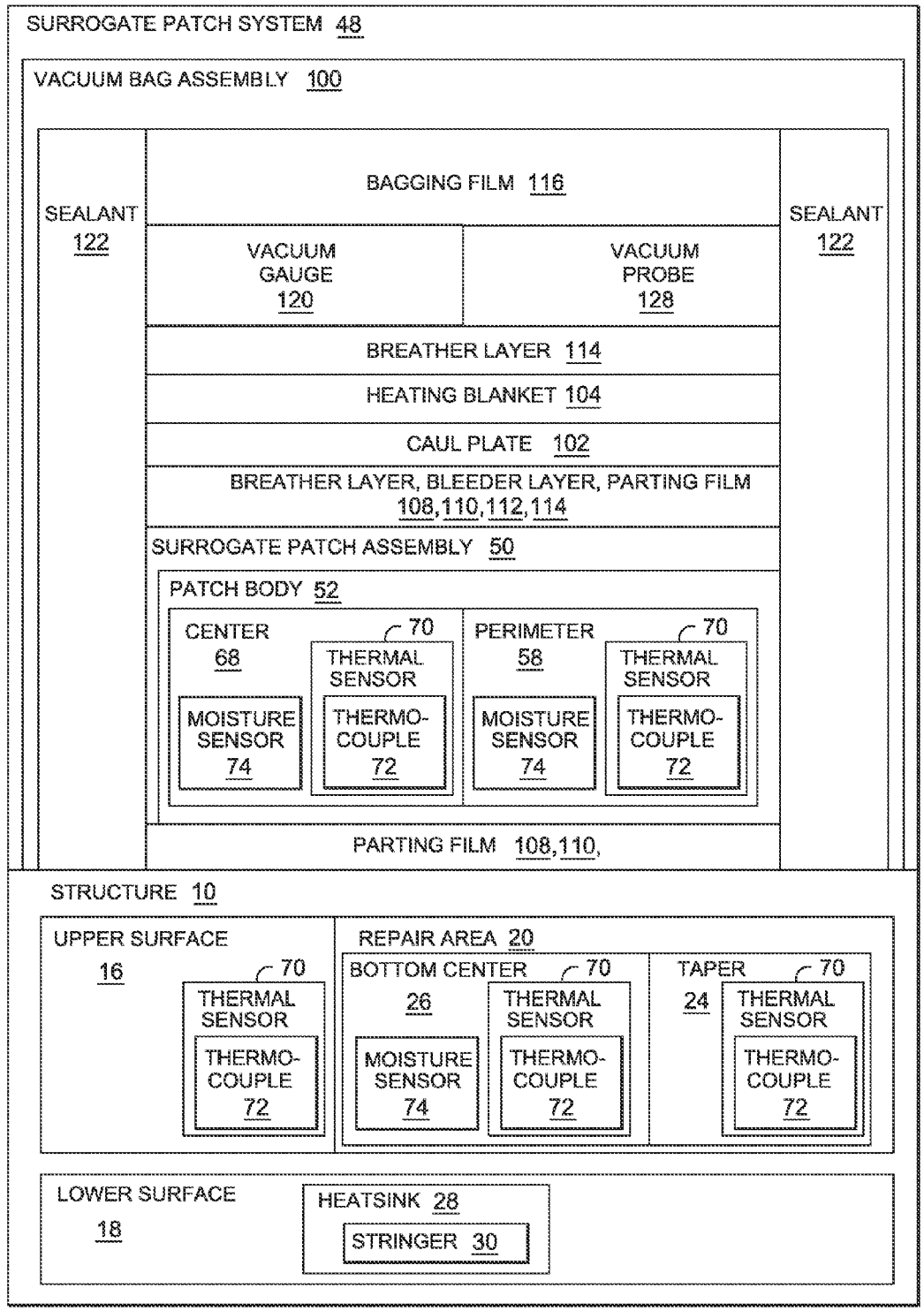
FIG. 9 is a block diagram of a surrogate patch system.

Referring briefly to FIG. 9, shown is a block diagram illustrating a surrogate patch system 48 as may be used for conducting a thermal survey and/or a moisture removal process. As can be seen in FIG. 9, the surrogate patch system 48 may comprise a vacuum bag assembly 100 which may include a bagging film 116 mounted to the structure 10 by means of sealant 122. The bagging film 116 may envelope a number of layers such as a breather layer 114, heating blanket 104, caul plate 102, bleeder layer 112, parting film 108, 110, as well as the surrogate patch assembly 50 comprising the surrogate patch body 52. The surrogate patch body 52 may have a patch center 68 and a perimeter 58. One or more sensors such as moisture sensors 74 or thermal sensors 70 (i.e., thermocouples 72) may be mounted to the surrogate patch body 52 such as along the perimeter 58 and/or patch center 68 or embedded within the surrogate patch body 52. The surrogate patch body 52 may be mounted in the rework area 20 and may be separated therefrom by means of the parting film. The rework area 20 may be formed in the structure 10 such as along an upper surface 16 thereof. The rework area 20 may include the bottom center 26 within which a sensor such as a moisture sensor 74 and/or a thermal sensor 70 (i.e., thermocouple) may be mounted. Likewise, one or more sensors such as thermal sensors 70 may be mounted on a scarf 24 of the rework area 20. Likewise, the upper surface 16 of the structure 10 surrounding the rework area 20 may include thermal sensors 70 such as thermocouples 72 in order to identify temperature variations that may occur as a result of heat drawn from the rework area 20 by heat sinks 28 such as stringers 30.

Figure 10:
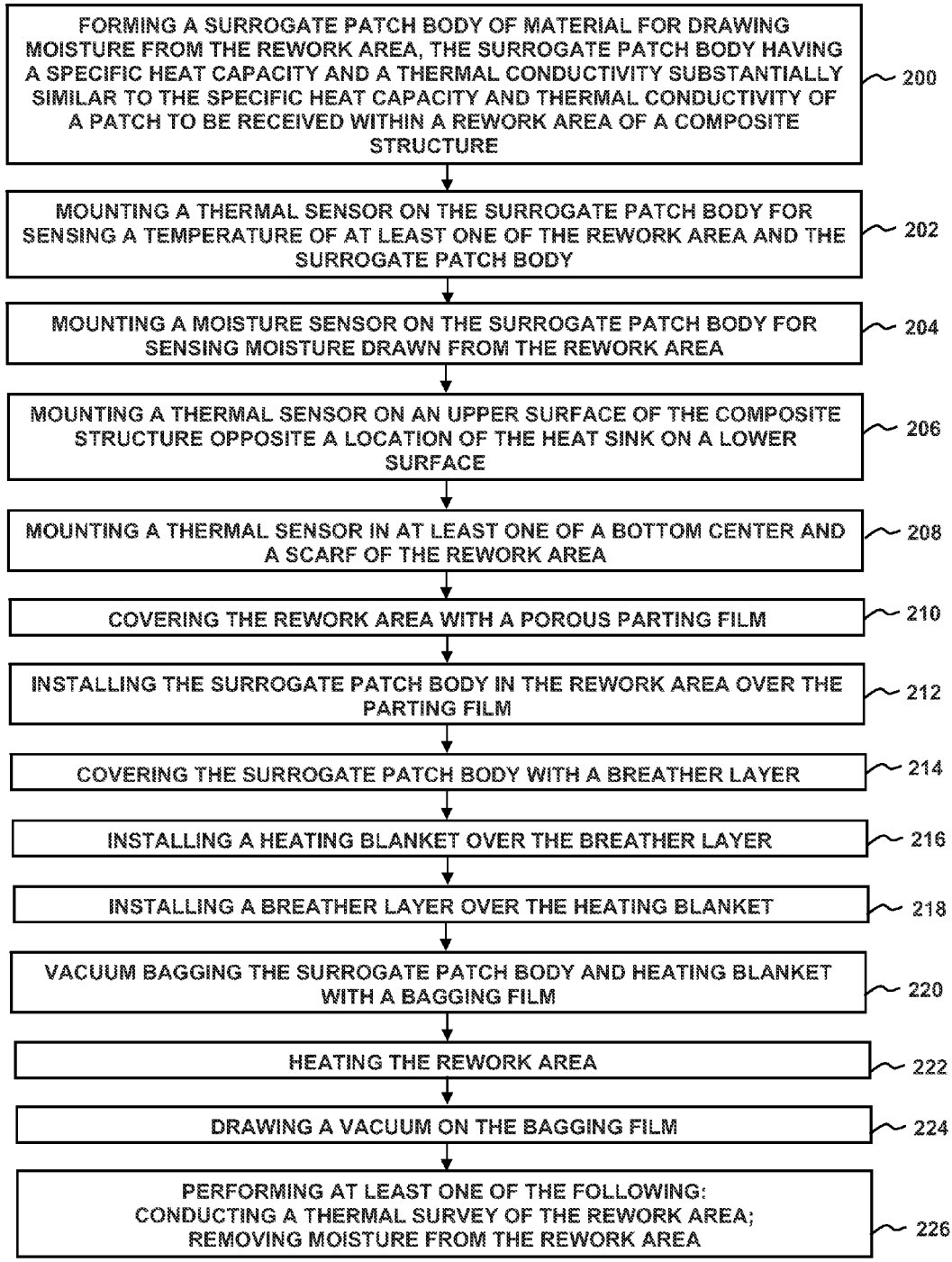
FIG. 10 is an illustration of a flow diagram for a methodology for repairing a composite structure.

Referring to FIG. 10, shown is an illustration of a flow diagram for a methodology for repairing a structure such as a composite structure having a rework area. The structure may include upper and lower surfaces and may include at least one heat sink which may be disposed at a location relative to the rework area such as on a lower surface of the structure adjacent to the rework area. The method may comprise step 200 including forming the surrogate patch body which may optionally be formed and shaped complementary to the shape of the rework area. For example, the surrogate patch body may be formed of woven or non-woven material for drawing moisture from the rework area. The surrogate patch body may have top and bottom surfaces and is preferably formed of a material for drawing moisture from the rework area such as during a moisture removal process. Furthermore, the surrogate patch body preferably has thermal properties that are substantially similar to or complementary to the thermal properties of composite material from which the final patch may be formed.

For example, the surrogate patch body may have a specific heat capacity and/or a thermal conductivity that is substantially equivalent to a specific heat capacity and/or thermal conductivity of epoxy pre-impregnated carbon fiber tape and fabric. However, the thermal properties of the composite material may comprise thermal properties of any composite material and are not limited to epoxy prepregs or carbon fiber tapes but may include non-pre-impregnated and/or wet layup material systems. As described above, the surrogate patch body may include at least one thermal sensor which may be mounted on the surrogate patch body on the top surface, the bottom surface or which may be embedded within the surrogate patch body or any combination of the above. The surrogate patch body may further include at least one moisture sensor which may be mounted on the surrogate patch body at any location such as on a patch center or along a perimeter of the surrogate patch body or a combination of such locations.

Referring still to FIG. 10, step 202 may comprise mounting one or more thermal sensors on the surrogate patch body for sensing the temperature of the rework area and/or the surrogate patch body. For example, thermal sensors such as, without limitation, thermocouples may be mounted on the top and/or bottom surfaces of the surrogate patch body. Thermal sensors may optionally be embedded within the surrogate patch body as is illustrated in FIG. 4 and described above. Thermal sensors on the bottom surface of the surrogate patch body may monitor the temperature of the rework area and/or the temperature of the surrogate patch body. Step 204 may comprise mounting one or more moisture sensors on the surrogate patch body for sensing moisture that may be drawn from the rework area into the surrogate patch body. In this regard, the surrogate patch body may be formed of any material having a relatively high moisture-absorbing capability as indicated above. In this regard, the surrogate patch body may be formed of materials having relatively high absorbency at the elevated temperatures associated with processing of composite materials.

Referring still to FIG. 10, step 206 may include mounting one or more thermal sensors on the upper surface of the composite structure. For example, thermal sensors may be mounted on the upper surface of the composite structure opposite the location of one or more heat sinks which may be disposed adjacent to the bottom surface of the composite structure or at any location on the upper surface. Step 208 may comprise mounting one or more of the thermal sensors in the rework area such as in the bottom center of the rework area and/or on the scarf (i.e., taper angle) of the rework area for monitoring temperatures in the rework area. Step 210 in the methodology of repairing the structure may include covering the rework area with a porous parting film such as fluorinated ethylene propylene (FEP) or any other suitable film material for preventing contact of the surrogate patch body with the composite structure and rework area. However, it is contemplated that the material from which the surrogate patch body is formed may obviate the need for a parting film.

Step 212 may include installing the surrogate patch assembly into the rework area such as on top of the porous and/or non-porous parting film. For example, the surrogate patch may be installed in a manner illustrated in FIG. 8 wherein the surrogate patch body may be formed as a substantially constant thickness unitary or single-layer structure which is substantially conformable to the shape and/or contour of the rework area. Alternatively, the surrogate patch body may be formed of a plurality of layers arranged in stacked formation as illustrated in FIG. 4 and wherein the layers of material which make up the surrogate patch body are conformable or resiliently flexible or compressible in order to allow for conforming the surrogate patch body to the contour or shape of the rework area.

Referring still to FIG. 10, step 214 of the methodology may further include covering the surrogate patch body and rework area with a breather layer to facilitate the substantially uniform application of vacuum pressure to the surrogate patch body. The method may further include the step of installing a heating blanket or other suitable heating equipment in step 216 and as is illustrated in FIGS. 7 and 8. The heating blanket may facilitate the heating of the rework area and the surrogate patch body during the thermal survey and/or during the moisture removal process. A caul plate 102 (FIG. 7) may optionally be included between the breather layer and the heating blanket 104 as illustrated in FIG. 7 in order to provide uniform pressure distribution to the surrogate patch body.

Step 218 of FIG. 10 may comprise installing a breather layer over the heating blanket as illustrated in FIG. 7 followed by vacuum bagging in step 220 such that the surrogate patch body and heating blanket are enveloped by the bagging film which may be sealed to the top surface of the composite structure 10 as illustrated in FIG. 8. Vacuum may be applied via the vacuum probe illustrated in FIG. 8 in order to draw a vacuum on the bagging film which may be monitored by means of a vacuum gauge installed as illustrated in FIG. 8. Heat may be applied such as by the heating blanket in step 222 during the drawing of the vacuum in step 224 such that the thermal survey and/or moisture removal process may be performed on the rework area in step 226.

The thermal survey process may be similar to that which is conventionally performed wherein the rework area may be heated and the temperature monitored. Depending on the temperature measurements, insulation may be locally added to areas of the composite structure such as adjacent to heat sinks or to other areas as indicated above in order to attain substantial temperature uniformity throughout the bondline. The heating of the rework area may also be adjusted by adjusting the heating blanket during the thermal survey to attain substantial temperature uniformity. The moisture removal process may comprise heating the rework area via the heating blanket and recording moisture data provided by moisture sensors mounted within the surrogate patch body. The moisture removal process may be performed prior to and/or during the thermal survey. Advantageously, the surrogate patch body configuration may facilitate the performance of the thermal survey and the moisture removal process in a manner that may eliminate an additional heat cycle typically required in separate thermal survey and moisture removal processes of conventional pre-repair operations.

In an embodiment, the moisture removal process may comprise weighing the surrogate patch body prior to installation into the rework area. Upon the completion of the thermal survey and/or moisture removal process, the surrogate patch body may again be weighed to determine the moisture absorption level which may then be correlated to the moisture content of the rework area. More specifically, the moisture removal process may comprise weighing the surrogate patch body prior to installing the surrogate patch body into the rework area and vacuum bagging the surrogate patch body. The method may include heating the rework area after drawing a vacuum on the bagging film. Alternatively, the heating blanket may be omitted and the composite structure may be heated via an oven or in an autoclave. During heating, the temperature of the rework area may be monitored using data from the thermal sensors. The heating may result in drying (i.e., moisture removal) of the rework area of the composite structure. The surrogate patch body of the surrogate patch assembly may be removed from the rework area and may be weighed in order to determine the amount of moisture drawn out of the rework area.

Figure 11:
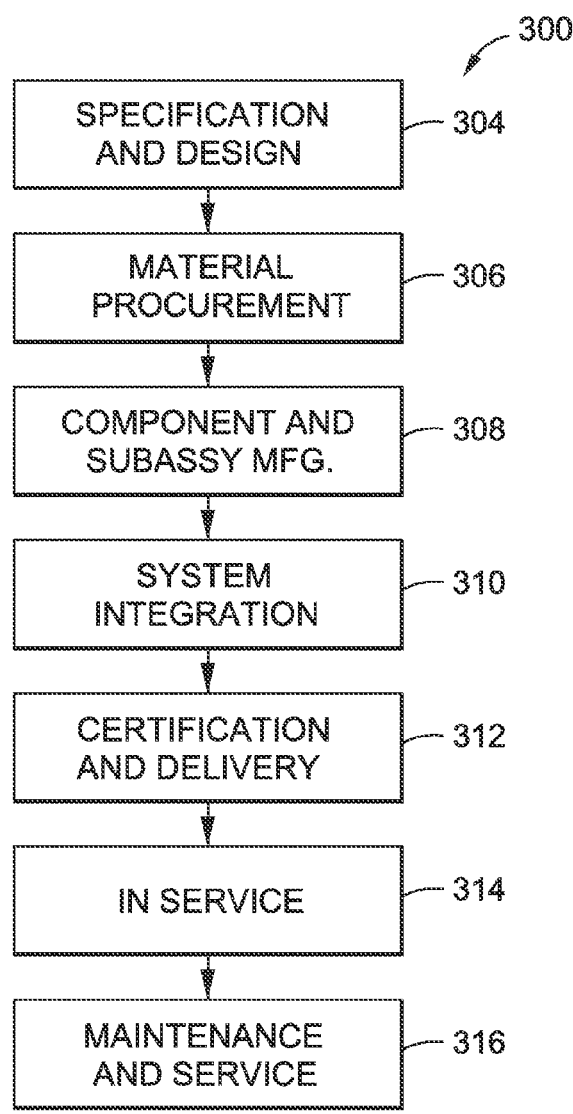
FIG. 11 is a flow diagram of an aircraft production and service methodology.
Figure 12:
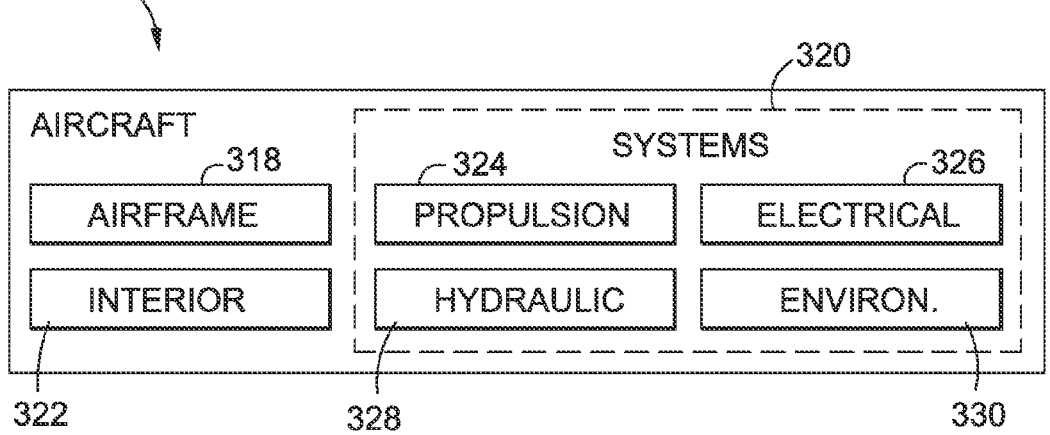
FIG. 12 is a block diagram of an aircraft.

Referring to FIGS. 11-12, embodiments of the disclosure may be described in the context of an aircraft manufacturing and service method 300 as shown in FIG. 11 and an aircraft 302 as shown in FIG. 12. During pre-production, exemplary method 300 may include specification and design 304 of the aircraft 302 and material procurement 306. During production, component and subassembly manufacturing 308 and system integration 310 of the aircraft 302 takes place. Thereafter, the aircraft 302 may go through certification and delivery 312 in order to be placed in service 314. While in service by a customer, the aircraft 302 is scheduled for routine maintenance and service 316 (which may also include modification, reconfiguration, refurbishment, and so on).

Each of the processes of method 300 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 12, the aircraft 302 produced by exemplary method 300 may include an airframe 318 with a plurality of systems 320 and an interior 322. Examples of high-level systems 320 include one or more of a propulsion system 324, an electrical system 326, a hydraulic system 328, and an environmental system 330. Any number of other systems may be included. Although an aerospace example is shown, the principles of the disclosed embodiments may be applied to other industries, such as the automotive industry.

Apparatus and methods embodied herein may be employed during any one or more of the stages of the production and service method 300. For example, components or subassemblies corresponding to production process 308 may be fabricated or manufactured in a manner similar to components or subassemblies produced while the aircraft 302 is in service. Also, one or more apparatus embodiments, method embodiments, or a combination thereof may be utilized during the production stages 308 and 310, for example, by substantially expediting assembly of or reducing the cost of an aircraft 302. Similarly, one or more of apparatus embodiments, method embodiments, or a combination thereof may be utilized while the aircraft 302 is in service, for example and without limitation, to maintenance and service 316.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A surrogate patch assembly for a rework area of a structure, comprising:
   a surrogate patch body formed of a material for drawing moisture from the rework area of a composite structure, the surrogate patch body being non-bonded to the rework area and being removed from the rework area prior to permanent bonding of a final patch to the rework area; and
   at least one sensor mounted to the surrogate patch body and being configured as one of the following:
      a thermal sensor for sensing a temperature of at least one of the rework area and the surrogate patch body; and
      a moisture sensor for sensing moisture in the surrogate patch body.

2. The surrogate patch assembly of claim 1 wherein:
   the moisture sensor comprises at least one of a moisture detection strip and an electrochemical impedance spectroscopy (EIS) sensor.

3. The surrogate patch assembly of claim 1 wherein:
   the surrogate patch body includes a top surface having a plurality of moisture sensors surrogate thereon.

4. The surrogate patch assembly of claim 1 wherein:
   the surrogate patch body has top and bottom surfaces, at least one of the sensors being mounted in one of the following locations: the top surface, the bottom surface, embedded within the surrogate patch body between the top and bottom surfaces.

5. The surrogate patch assembly of claim 1 wherein:
   the surrogate patch body comprises a plurality of layers;
   at least one of the sensors being interposed between a pair of the layers.

6. The surrogate patch assembly of claim 1 wherein:
   the material comprises one of natural and synthetic material including at least one of the following: wool, cotton, silk, linen, polyester, nylon, acrylic.

7. The surrogate patch assembly of claim 6 wherein:
   the material comprises felt.

8. The surrogate patch assembly of claim 1 wherein:
   the surrogate patch body is conformable in three-dimensions such that the surrogate patch body is conformable to the rework area.

9. The surrogate patch assembly of claim 1 wherein:
   the rework area is configured to receive a patch;
   the surrogate patch body having a specific heat capacity and a thermal conductivity that is substantially equivalent to at least one of the specific heat capacity and thermal conductivity of the patch.

10. The surrogate patch assembly of claim 9 wherein:
    the surrogate patch body is formed of material having a thermal conductivity in the range of from approximately 0.01 W/mK to approximately 1.0 W/mK.

11. The surrogate patch assembly of claim 9 wherein:
    the surrogate patch body is formed of material having a specific heat capacity in the range of from approximately 600 J/(kgK) to approximately 1100 J/(kgK).

12. A surrogate patch assembly for a rework area of a composite structure, comprising:
    a surrogate patch body being non-bonded to a rework area of a composite structure and being removed from the rework area prior to permanent bonding of a final patch to the rework area, the surrogate patch body having top and bottom surfaces and defining a substantially uniform thickness, the surrogate patch body being formed of felt for drawing moisture from the rework area, the felt having a thermal conductivity of approximately 0.01 to 1.0 W/mK and a specific heat capacity of approximately 600 to 1100 J/(kgK);

a plurality of thermal sensors mounted to the surrogate patch body for sensing a temperature of the rework area and the surrogate patch body, at least one of the thermal sensors being embedded within the surrogate patch body between the top and bottom surfaces; and a plurality of moisture sensors mounted to the surrogate patch body on the top surface for sensing moisture absorbed from the rework area.

13. A surrogate patch system for repairing a structure with a patch receivable within a rework area, the system comprising:

a surrogate patch body being non-bonded to a rework area of a composite structure and being removed from the rework area prior to permanent bonding of a final patch to the rework area, the surrogate patch body being formed of non-composite material having thermal properties substantially similar to thermal properties of the patch, the thermal properties comprising at least one of specific heat capacity and thermal conductivity;

at least one thermal sensor mounted on the surrogate patch body for sensing a temperature of the surrogate patch body; and at least one thermal sensor mounted on the rework area for sensing a temperature of the rework area.

14. The surrogate patch system of claim 13 wherein the surrogate patch body has at least one of the following thermal properties:

a thermal conductivity in the range of from approximately 0.01 W/mK to approximately 1.0 W/mK;

a specific heat capacity in the range of from approximately 600 J/(kgK) to approximately 1100 J/(kgK).

15. The surrogate patch system of claim 13 wherein:
the surrogate patch body is formed of a material for drawing moisture from the rework area.

16. The surrogate patch system of claim 13 wherein:
the surrogate patch body includes a plurality of moisture sensors mounted thereon.

17. The surrogate patch system of claim 16 wherein:
the surrogate patch body comprises a plurality of layers;
at least one of the thermal sensor and moisture sensors being interposed between a pair of the layers.

18. The surrogate patch system of claim 13 wherein the structure includes upper and lower surfaces and having at least one heat sink mounted on the lower surface adjacent to the rework area, the system further comprising:

at least one thermal sensor mounted on the upper surface opposite the location of the heat sink on the bottom surface.

19. A method of repairing a composite structure using a surrogate patch assembly as claimed in claim 1, the composite structure comprised of a plurality of plies and having the rework area for receiving the final patch, the method comprising the steps of:

forming the surrogate patch body of material having a specific heat capacity and a thermal conductivity substantially similar to the specific heat capacity and thermal conductivity of the final patch;

mounting the thermal sensor on the surrogate patch body;
mounting the moisture sensor on the surrogate patch body;
installing the surrogate patch body in the rework area; and
performing at least one of the following:
conducting a thermal survey of the rework area;
removing moisture from the rework area.

* * * * *